(12) United States Patent
Tabada et al.

(10) Patent No.: US 9,498,617 B2
(45) Date of Patent: Nov. 22, 2016

(54) CONFORMALLY ENCAPSULATED MULTI-ELECTRODE ARRAYS WITH SEAMLESS INSULATION

(71) Applicants: Melody Tabada; Kedar G. Shah, Oakland, CA (US); Vanessa Tolosa, Oakland, CA (US); Satinderall S. Pannu, Pleasanton, CA (US); Angela Tooker, Dublin, CA (US); Terri Delima, Livermore, CA (US); Heeral Sheth, Oakland, CA (US); Sarah Felix, Oakland, CA (US)

(72) Inventors: Phillipe J. Tabada, Roseville, CA (US); Kedar G. Shah, Oakland, CA (US); Vanessa Tolosa, Oakland, CA (US); Satinderall S. Pannu, Pleasanton, CA (US); Angela Tooker, Dublin, CA (US); Terri Delima, Livermore, CA (US); Heeral Sheth, Oakland, CA (US); Sarah Felix, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 109 days.

(21) Appl. No.: 13/792,708

(22) Filed: Mar. 11, 2013

(65) Prior Publication Data
US 2013/0345780 A1  Dec. 26, 2013

Related U.S. Application Data

(60) Provisional application No. 61/661,751, filed on Jun. 19, 2012.

(51) Int. Cl.
*A61N 1/04* (2006.01)
*A61N 1/05* (2006.01)
(Continued)

(52) U.S. Cl.
CPC .............. *A61N 1/04* (2013.01); *A61N 1/0529* (2013.01); *A61B 5/04001* (2013.01);
(Continued)

(58) Field of Classification Search
CPC ............ A61N 1/02; A61N 1/04; A61N 1/05; A61N 1/08; A61N 1/16; A61N 1/18; A61N 1/025; A61N 1/0404; A61N 2001/083; A61N 2001/086; A61N 1/34; A61N 1/325; A61N 1/327; A61N 1/372; A61N 1/3605; A61N 1/36014; A61N 1/36021; A61N 1/36071; A61N 1/37205; H01L 39/2429; A61K 8/044; A61K 49/0076; A61K 49/0461; A61K 49/1806; A61K 49/226; A61K 51/1217
See application file for complete search history.

(56) References Cited

U.S. PATENT DOCUMENTS

5,720,099 A    2/1998  Parker et al.
7,914,842 B1   3/2011  Greenberg et al.
(Continued)

*Primary Examiner* — Carl H Layno
*Assistant Examiner* — Elizabeth K So
(74) *Attorney, Agent, or Firm* — James S. Tak (57) ABSTRACT

Thin-film multi-electrode arrays (MEA) having one or more electrically conductive beams conformally encapsulated in a seamless block of electrically insulating material, and methods of fabricating such MEAs using reproducible, microfabrication processes. One or more electrically conductive traces are formed on scaffold material that is subsequently removed to suspend the traces over a substrate by support portions of the trace beam in contact with the substrate. By encapsulating the suspended traces, either individually or together, with a single continuous layer of an electrically insulating material, a seamless block of electrically insulating material is formed that conforms to the shape of the trace beam structure, including any trace backings which provide suspension support. Electrical contacts, electrodes, or leads of the traces are exposed from the encapsulated trace beam structure by removing the substrate.

7 Claims, 10 Drawing Sheets

(51) Int. Cl.
  *A61K 8/04* (2006.01)
  *A61K 49/18* (2006.01)
  *A61K 51/12* (2006.01)
  *A61B 5/04* (2006.01)

(52) U.S. Cl.
  CPC . *A61B 2562/0209* (2013.01); *A61B 2562/046* (2013.01); *A61B 2562/125* (2013.01); *A61K 8/044* (2013.01); *A61K 49/1806* (2013.01); *A61K 51/1217* (2013.01); *A61N 1/0551* (2013.01)

(56) References Cited

U.S. PATENT DOCUMENTS

| 8,183,111 | B1 | 5/2012 | Tabada et al. |
| 2011/0034977 | A1 | 2/2011 | Janik et al. |
| 2012/0048733 | A1 | 3/2012 | Yu et al. |

CONFORMALLY ENCAPSULATED MULTI-ELECTRODE ARRAYS WITH SEAMLESS INSULATION

CLAIM OF PRIORITY IN PROVISIONAL APPLICATION

This patent document claims the benefit and priority of U.S. Provisional Application No. 61/661,751, filed on Jun. 19, 2012, hereby incorporated by reference.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to multi-electrode arrays (MEA) and fabrication methods thereof, and more particularly to a conformally encapsulated MEA and method of fabricating the MEA while in a suspended state over a substrate to conformally encapsulate the MEA in a seamless block of insulating material.

BACKGROUND OF THE INVENTION

Neural probes and interfaces are an essential tool in neuroscience. They typically comprise a multi-electrode array (MEA) configuration with exposed metal pads or electrodes located on rigid silicon shanks and connected, via interconnection traces, to output leads or to signal processing circuitry on a monolithic substrate. The exposed metal pads/electrodes provide a direct electrical interface with the neurons of a biological entity's nervous system to stimulate and/or record neural activity. Such neural probes enable researchers and clinicians to better explore and understand neurological diseases, neural coding, neural modulations, and neural topologies, as well as treat debilitating conditions of the nervous system. Moreover, implantable neural probes and interfaces in particular enable extended interaction with neural tissue. However, such probes and devices typically require invasive surgeries for implantation, and also often require additional surgeries to remove and replace devices that have failed or otherwise require maintenance or servicing. The medical industry continues to search for methods to improve patient comfort and device reliability, including developing methods to reduce the size and extend the lifetime of chronically implanted devices.

Standard polymer-based MEAs are made using multiple layers of polymers coated layer by layer (typically by spin-coating) after each metal film deposition and patterning, to insulate the patterned conductive wiring and lines. However, the multiple polymer-polymer and polymer-metal interfaces provide opportunities for water and solution infiltration leading to delamination and separation of the polymer layers. Penetration of bodily fluids at these compromised areas can result in trace metal corrosion, electrical shorts between interconnects, and ultimately device failure. Therefore, maintaining adequate adhesion between adjacent layers of polymer and polymer-metal layers is a consistent concern using this approach, and one of the reasons thin-film microelectrode arrays have been unsuccessful for long term implantation.

Previous attempts to solve the delamination problem for such polymer-based MEAs have included various polymer treatment methods to alter the physical or chemical properties of the polymer layers to improve adhesion therebetween. However, these methods have largely failed by either not providing sufficient improvements in adhesion, or the polymer treatment parameters required for effective adhesion is detrimental to the metal thin films. What is needed therefore is a durably insulated polymer-based MEA, and a method of fabricating such MEAs using reproducible microfabrication processes which extends operational lifetime by reducing the number and area of interfaces of the MEA that can be infiltrated and thereby reducing the opportunities for failure.

SUMMARY OF THE INVENTION

One aspect of the present invention includes a method of fabricating an electrode array, comprising: suspending at least one thin-film electrically conductive trace beam(s) over a substrate, wherein the trace beam(s) is suspended by at least one support portion(s) thereof in contact with the substrate; encapsulating the trace beam(s) with an electrically insulating material; and removing the substrate to expose an electrically conductive surface of the support portion(s) of the encapsulated trace beam(s).

Another aspect of the present invention includes an electrode array comprising: at least one thin-film electrically conductive trace beam(s) encapsulated in a seamless block of electrically insulating material except an electrically conductive surface of at least one support portion(s) of the encapsulated trace beam(s) is exposed through the electrically insulating material.

Generally, the present invention is directed to multi-electrode arrays (MEA) (e.g. microelectrode arrays with micron-sized features) with one or more electrically conductive beams conformally encapsulated in a seamless block of electrically insulating material, and methods of fabricating such MEAs using reproducible, high throughput, thin-film micro-fabrication processes. The fabrication method may be utilized to make MEA devices in a variety of structures, e.g., device shapes, number of metal layers, number of electrodes. For example, the encapsulated MEA device may be used as neural interfaces for a variety of applications in peripheral and cortical nerve stimulation and recording, including as a chronic, fully-implanted neural interface capable of extended operational lifetime due to reduced modes of failure through interface delamination.

In particular, the fabrication method generally includes first suspending one or more electrically conductive trace beams over a substrate by support portions of the trace beam in contact with the substrate. Suspension of the trace beam may be performed in various ways. In one example embodiment, the trace beam or beams may be suspended by selectively removing the underlying material, i.e. scaffold material upon which the trace beam is formed, from underneath the trace beams while the support portion or portions of the trace beams remain in contact with the substrate. In particular, the scaffold material may be a portion, e.g. a sacrificial layer, of the substrate upon which a trace beam is formed. In this manner, selective removal of the underlying material upon which the trace beam is formed, while keeping the support portion or portions of the trace beam in contact with the substrate, leaves behind the trace beam as a free-standing suspended beam that is suspended over the substrate.

To aid in suspension, a trace backing or backings may be formed on a single side or opposite sides of a trace beam, so as to provide single or double-sided suspension support. Such trace backings may be used to suspend single trace beams individually or a stack of trace beams in a multi-tier trace beam stack. Furthermore, the trace backings may be patterned to facilitate encapsulation. The trace backings may be made of, for example, polymers; other insulating materials such as for example ceramics, oxides, nitrides, glasses; or semiconductors such as for example silicon carbide and silicon. And various types of polymers may be used, including for example: polyimides, parylene, polyurethanes, polycarbonates, polymers that are vapor-deposited or spin-on liquids, and shape memory polymers.

It is appreciated that traces are the conductive lines or pathways of electronic circuits which extend and communicate between contact terminals, pads, or electrodes. In the present invention, the trace beam is characterized as a trace having a beam structure that is suitably rigid (either by itself or with reinforcement) to be laterally suspended as a suspension beam, either by a single cantilevered support structure, or multiple support structures. When the trace beam or beams is suspended over the substrate, it may be characterized as having a suspension span portion and a support portion or portions supporting the beam on the substrate upon which the trace beam is formed, similar to a bridge. It is notable that the support portion also forms the electrodes or electrical contacts when exposed in a subsequent step. And the trace beam may be formed and patterned from an electrically conductive layer or film, preferably a thin film metal layer. It is appreciated that various types of materials may be used for the trace beam, including for example: gold, titanium, platinum, iridium, Pt—Ir, Pt-black, iridium-oxide, Ti—Pt alloys, titanium nitride, chrome and aluminum, as well as other metals, conducting polymers, and conductive doped dielectrics. And various deposition methods are possible, including evaporation and or sputtering.

While in the suspended state, the trace beams are encapsulated, either individually or together, with a single continuous layer, film, or coating of an electrically insulating material, such as for example ceramics, oxidized metals, dielectrics, polymers. In particular materials that may be vapor-deposited may be used, such as for example polyimides, parylene, polyurethanes, polycarbonates. Because the trace beam is encapsulated while suspended, the single insulating layer forms a seamless block of electrically insulating material that conforms to the shape of the trace beam structure, including any trace backings which provide suspension support. By encapsulating the conductive traces and electrodes of the array with a single coating of an insulator, multiple-layered polymers are eliminated, along with the associated delamination concerns at the polymer-polymer interfaces/seams and polymer-metal interfaces/seams when exposed to external fluids, thereby reducing opportunities for failure.

One advantage of this method of directly encapsulating the trace structure with a polymer or other insulating material is that the entire surface of the suspended structure can be treated with an adhesion promoting material to enhance adhesion between itself and the encapsulating material. This may involve either treating the surface of bare suspended metal traces, or treating a composite of trace metal and backing material that make up the suspended structure. Adhesion promoters may also be applied in between the trace metal and backing material that make up the suspended structure. For example, an adhesion promoter can be applied to the suspended traces that promotes covalent bonds with a polymer that is cured directly onto the metal. Or, an intermediate metallic layer can be deposited on the traces onto which the encapsulating material will adhere better. Adhesion-promoting materials include metals (e.g. titanium, titanium-nitride, chrome), dielectrics (e.g. silicon dioxide, silicon nitride) or organic and non-organic (e.g. organic and non-organic chemicals with the appropriate chemical groups to adhere the trace and electrode material to the trace backing and the encapsulation polymer) adhesion promoters. The adhesion-promoting layer may be deposited using vapor deposition, spin coating, atomic layer deposition, or oxidation (but not limited to these techniques).

The following are some examples of treatments that can improve adhesion between different layers: (1) the adhesion promoter A-174 silane may be vapor deposited onto the suspended structure to promote adhesion of parylene that is subsequently deposited as the encapsulating material; (2) the trace metal may consist of a stack of metals, with the outer (top and bottom) layers being a metal such as titanium onto which the encapsulating material will adhere better; (3) the liquid adhesion promoter, HD Microsystems VM-652, may be applied on top of the trace metal film to enhance adhesion of a polyimide layer that is subsequently spin-deposited to create a backing layer; (4) in the case of a backing structure that consists of a top and bottom layer of polyimide, the bottom polyimide layer may be treated with KOH followed by HCl in order to create a surface layer of polyamic acid. Then, this surface layer will cure (i.e. convert back to polyimide) together with the top layer of polyimide, improving adhesion between the two layers.

After encapsulation, electrical contacts, electrodes, or leads of the traces are then exposed from the encapsulated trace beam structure by removing a substrate upon which the support portions of the trace beams are formed and connected. As such the substrate serves as the base foundation upon and over which the electrode array may be suspended, and conformally encapsulated while in a suspended state. And the substrate also serves to isolate/protect a surface of the support portion or portions of the trace beam from being encapsulated by the insulating material, only to expose the electrically conductive surface when it is separated/released from it. The electrically conductive surfaces of the support portions of the trace may be either an electrode site, or contact pads (leads) providing electrical connection to other devices/components.

BRIEF DESCRIPTION OF THE DRAWINGS

The accompanying drawings, which are incorporated into and form a part of the disclosure, are as follows.

DETAILED DESCRIPTION

Turning now to the drawings, FIGS. 1-5 show a first example embodiment of the method of fabricating a conformally encapsulated electrode array of the present invention, and the electrode array formed thereby.

Figure 1:
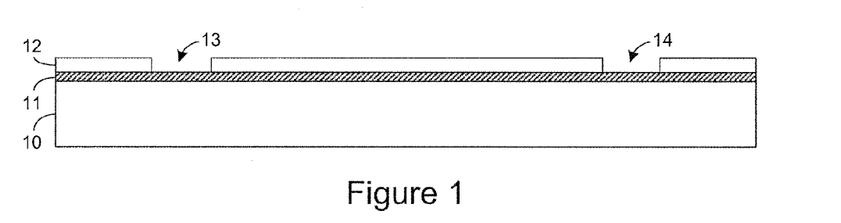
FIGS. 1-5 show the progression of fabricating a conformally encapsulated electrode array, in a first example embodiment of the method and apparatus of the present invention.

In particular, FIG. 1 shows a substrate having three layers, including a lower layer 10 which may be characterized as a handle wafer; a middle or embedded layer 11 which may be characterized as a release layer; and an upper layer 12 which may be characterized as a sacrificial layer. Via openings 13, 14 are also shown formed through the sacrificial layer 12 down to the release layer 11, such as for example by an etching process. It is appreciated that each of the release and sacrificial layers 11 and 12 may be formed using various deposition methods and techniques known in the microfabrication arts. In the alternative, preformed three layer substrates, such as silicon-on-insulator (SOI) wafers, may also be used. It is further appreciated that the sacrificial layer material may be selected from any number of materials that may be selectively removed over, i.e. in lieu of, the electrically conductive trace beam material 15. For example, the sacrificial material may be silicon or polysilicon that is dry etchable, or thermally decomposable sacrificial material, which decomposes, for example, at <350° C. The sacrificial material may also be a combination of, for example: organic and inorganic materials, such as a hydrocarbon-siloxane polymer hybrid; silicon-containing and carbonaceous materials; norbornene based photosensitive sacrificial materials; polypropylene carbonates; and shape memory polymers. Furthermore, the sacrificial material may be photoresist; metals different from the trace beam; or photosensitive polyimides or other polymers, for example. And the release layer may be photoresist or a thin film metal layer such as chromium as well as inorganics such as NaCl, MgF, etc.

Figure 2:
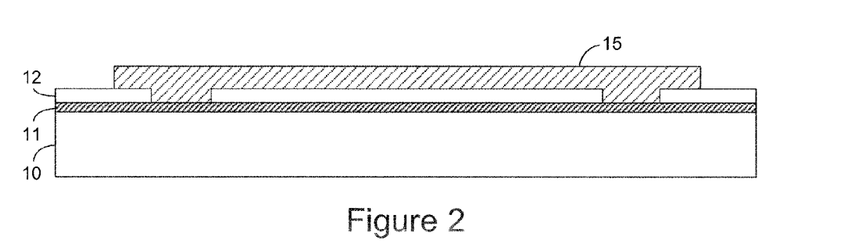

In FIG. 2, an electrically conductive trace beam 15 is shown formed on the sacrificial layer 12, with portions of the trace beam formed in the via openings 13, 14 (to form the support portions for suspending the beam as well as the electrodes/contact pads in subsequent steps). In particular, the trace beam 15 may be formed by depositing a metal layer on the sacrificial layer 12, as well as in the via openings 13, 14 and on the release layer 11, followed by patterning the metal layer into the trace beam 15 (which includes the portions deposited in the via openings), using various photolithographic and/or other known micro-fabrication techniques. Though only one is shown, it is appreciated that more than one trace beam may be formed and patterned on the sacrificial layer, and additional via openings provided in which the metal layer is deposited to become a part of the additional trace beam or beams. While the metal used to form the suspension span portion of the trace beam can be the same metal used to form the support portions (e.g. electrodes) as shown in FIG. 2, it is also appreciated that a separate electrode deposition step may be performed, prior to depositing the metal layer on the sacrificial layer, to deposit a separate conductive material (i.e. electrode metal) into the via openings to form (cast) electrodes.

Figure 3:
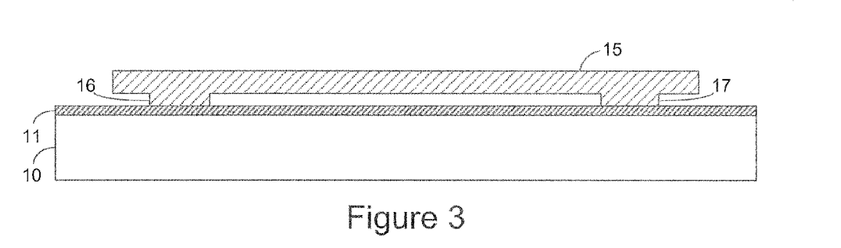

In FIG. 3, the sacrificial layer is shown removed from underneath a suspension-span or otherwise laterally-extending portion of the trace beam 15, so that the trace beam is suspended over the substrate, and in particular over the release layer 11 of the substrate, by support portions, which are shown as support legs or posts 16 and 17. In this embodiment, the metal trace is preferably formed with sufficient thickness that enables it to be suspended across its suspension span, without the need for suspension support e.g. reinforcement backing, brace, or spine. For example, a stack of trace metal 2 μm in thickness is typically sufficient to suspend 5 cm in length. A gold trace beam having a thickness of 2 μm has been shown capable of spanning 80 mm without contacting the substrate. The relationship between the trace metal thickness and contact with other traces or the substrate depend on the metals used, the residual stress in the metal, the length of the span, and other mechanical and electrical properties. And removal of the sacrificial material will depend on the sacrificial material type, as described in the Summary.

Figure 4:
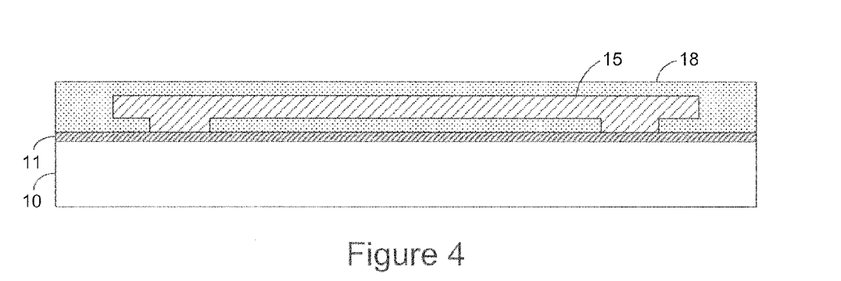

In FIG. 4, the suspended trace beam 15 is shown encapsulated with an insulating material 18, which may be for example a polymer. The encapsulating step may be performed using a vapor deposition process, as described in the Summary, to uniformly coat insulating material on all exposed surfaces. Due to the suspended state of the trace beam 15, the insulating material is conformally formed around all exposed surfaces of the trace beam such that a seamless block is formed from the single layer of insulating material, including underneath the suspension span of the trace beam, as shown. It is appreciated that other independently suspended trace beams (not shown), may also be individually conformally coated and encapsulated in a similar fashion. It is also appreciated that adhesion promoter may be deposited (e.g. by vapor deposition) to the trace beam (and the electrode material) to promote polymer-metal adhesion with the encapsulating/insulating material.

Figure 5:
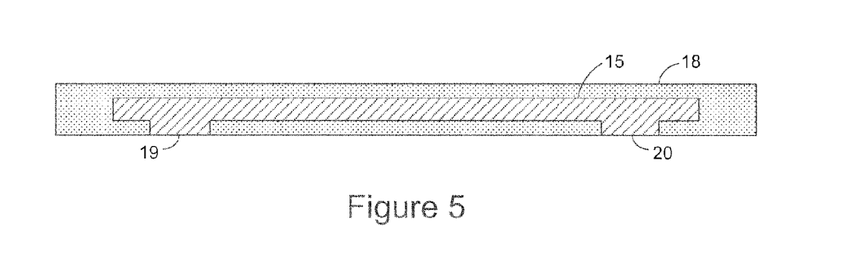

And in FIG. 5, the electrode array is shown released from the substrate. In particular, the substrate is removed along the release layer 11, to expose electrically conductive surfaces 19 and 20 of the support legs 16 and 17, respectively. The exposed conductive surfaces 19 and 20 may be, for example, an electrode and connector (for connecting to other electronics, for example), respectively. What remains is the electrode array having an electrically conductive trace beam encapsulated in a seamless block of electrically insulating material except an electrically conductive surface of the support legs being exposed through the electrically insulating material. As can be seen in FIG. 5, there is no polymer-polymer interface, and the only polymer-metal interface is limited to the electrode and connector openings.

FIGS. 6-9 show a second example embodiment of the method of fabricating a conformally encapsulated electrode array of the present invention, and the electrode array formed thereby. In particular, the progression of FIGS. 6-9 continues from the stage of fabrication shown in FIG. 2 and previously described.

Figure 6:
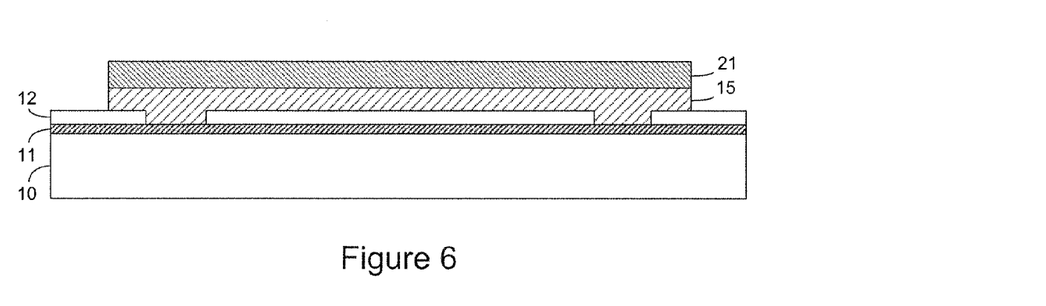
FIGS. 6-9 show the progression of fabricating a conformally encapsulated electrode array, in a second example embodiment of the method and apparatus of the present invention.
Figure 7:
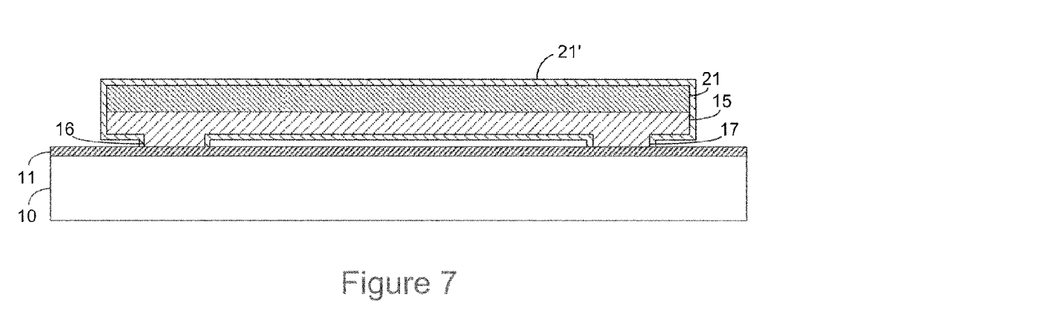

FIG. 6 shows a trace backing structure 21 formed on one side (top side) of the trace beam 15, to provide structural reinforcement support for the suspension span of the trace beam 15 when placed in suspension, as shown in FIG. 7. The trace backing structure may be a thin layer of polymer, other insulator, or semiconductor deposited on the thin-film metal trace.

In FIG. 7, removal of the sacrificial layer 12 from underneath a suspension-span or otherwise laterally-extending portion of the trace beam 15 suspends the trace beam 15 over the substrate, and in particular over the release layer 11 of the substrate, by support legs 16 and 17, similar to FIG. 3. Furthermore, an optional adhesion layer 21' is shown formed on the trace backing 21 as well as on the trace beam 15 including support legs 16 and 17, to promote adhesion between the trace beam structure and a polymer insulating/encapsulating material.

Figure 8:
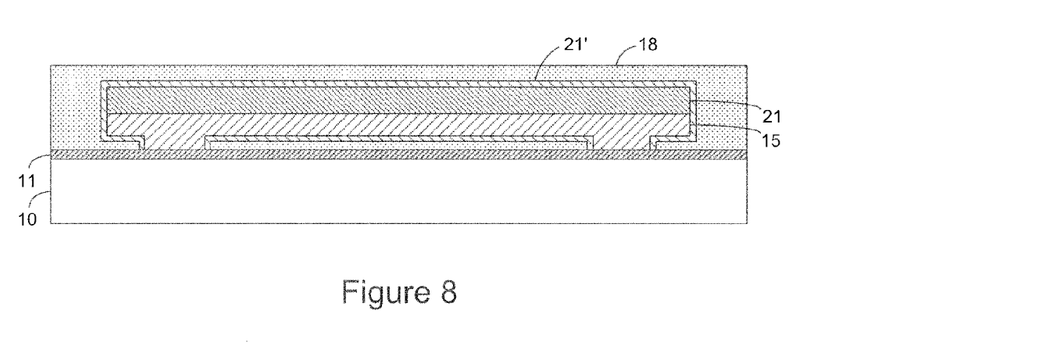

In FIG. 8, the reinforced and suspended trace beam 15, together with the trace backing 21 and adhesion layer 21', i.e. trace beam structure, is shown conformally encapsulated with an insulating material 18, which may be for example a polymer, similar to FIG. 4. Similar to FIG. 4, it is appreciated that other independently suspended trace beam structures (not shown), may also be individually conformally coated and encapsulated in a similar fashion.

Figure 9:
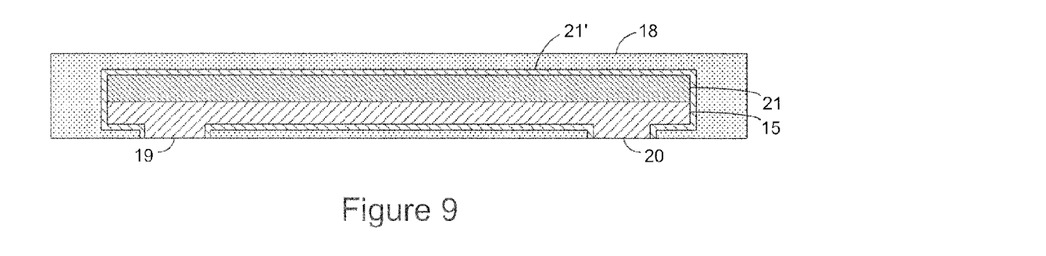

And FIG. 9 shows the electrode array released from the substrate, similar to FIG. 5 to expose electrically conductive surfaces 19 and 20 of the support legs 16 and 17, respectively. The electrode array has an electrically conductive trace beam encapsulated in a seamless block of electrically insulating material except an electrically conductive surface of the support legs being exposed through the electrically insulating material.

FIGS. 10-14 show a third example embodiment of the method of fabrication of the present invention to form a conformally encapsulated electrode array with double-sided backing support for suspending the trace during encapsulation.

Figure 10:
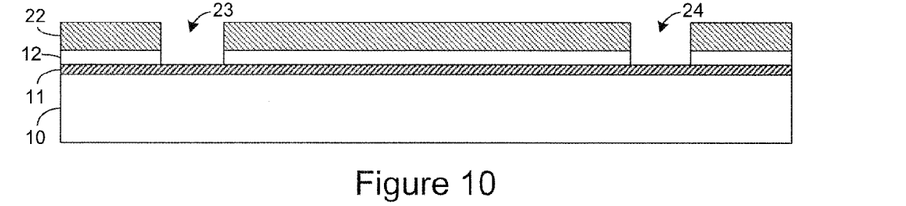
FIGS. 10-14 show the progression of fabricating a conformally encapsulated electrode array, in a third example embodiment of the method and apparatus of the present invention.

In particular, FIG. 10 shows a substrate having three layers, similar to FIG. 1, and including the lower layer 10, i.e. the handle wafer; the middle or embedded layer 11, i.e. the release layer; and the upper layer 12, i.e. the sacrificial layer. On the sacrificial layer 12 there is deposited a trace backing layer 22, which may be a polymer material of various types as previously described. Via openings 23, 24 are also shown formed through the trace backing layer 22 and the sacrificial layer 12 down to the release layer 11, such as for example by an etching process. As previously described the sacrificial layer may be selected from various types of materials that may be selectively removed over the electrically conductive trace beam material 15.

Figure 11:
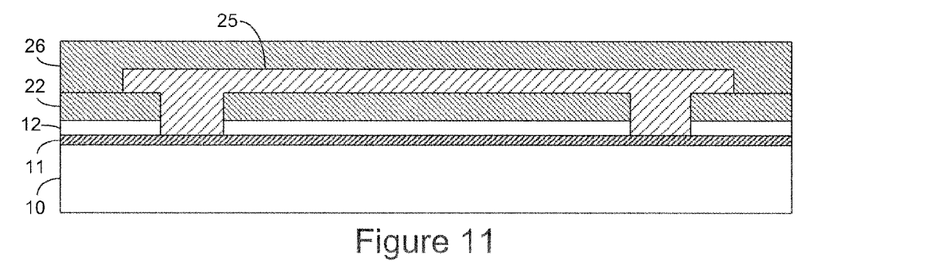

In FIG. 11, an electrically conductive trace beam 25 is shown formed on the trace backing layer 22, with portions of the trace beam also formed in the via openings 23, 24. In particular, the trace beam 25 may be formed by depositing a metal layer on the trace backing layer 22, as well as in the via openings 23, 24 and on the release layer 11. Another trace backing layer 26 is shown deposited on the trace beam 25, as well as on the first trace backing layer 22.

Figure 12:
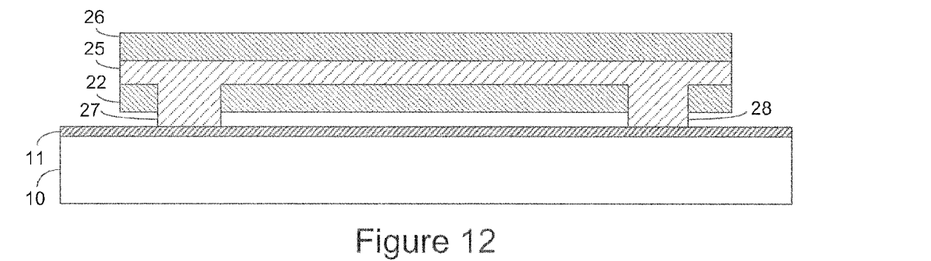

In FIG. 12, the trace back layers 22 and 26 and the metal layer 25 are shown patterned, using various photolithographic and/or other known micro-fabrication techniques, to form a trace beam structure (which includes the portions deposited in the via openings) having double sided suspension support from a lower trace backing and an upper trace backing on opposite sides of the suspension span portion of the trace beam. The double-reinforced trace beam structure is then suspended over the substrate by removing the sacrificial layer 12 from underneath a suspension-span or otherwise laterally-extending portion of the trace beam 25. In particular, the trace beam structure is shown suspended by support legs 27 and 28 which are in contact with the release layer 11.

Figure 13:
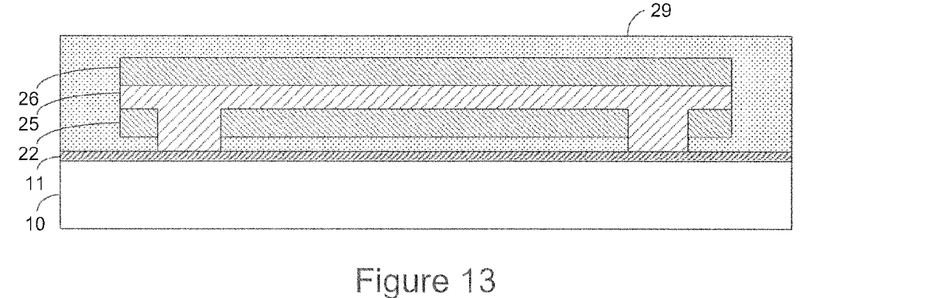

In FIG. 13, the reinforced and suspended trace beam structure, 22, 25, 26, is shown conformally encapsulated with an insulating material 29, which may be for example a polymer, similar to FIG. 4. And similar to FIG. 4, it is appreciated that other independently suspended trace beam structures (not shown), may also be individually conformally coated and encapsulated in a similar fashion.

Figure 14:
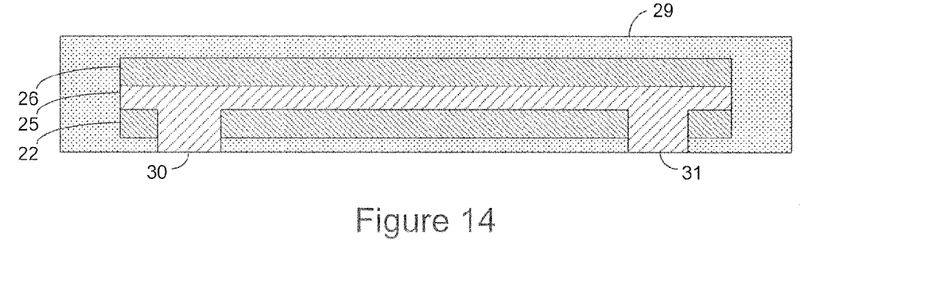

And FIG. 14 shows the electrode array released from the substrate, similar to FIG. 5 to expose electrically conductive surfaces 30 and 31 of the support legs 27 and 28, respectively. The electrode array has an electrically conductive trace beam encapsulated in a seamless block of electrically insulating material except an electrically conductive surface of the support legs being exposed through the electrically insulating material.

FIGS. 15-21 show the progression of fabricating a conformally encapsulated electrode array, in a fourth example embodiment of the method and apparatus of the present invention. In particular, the progression of FIGS. 6-9 continues from the stage of fabrication shown in FIG. 2 and previously described, and show multiple trace beams individually suspended (with or without suspension support/backing) and individually encapsulated. Furthermore, the individually conformally encapsulated trace beams may be joined together in another insulating material, such as silicone giving flexibility the electrode array.

Figure 15:
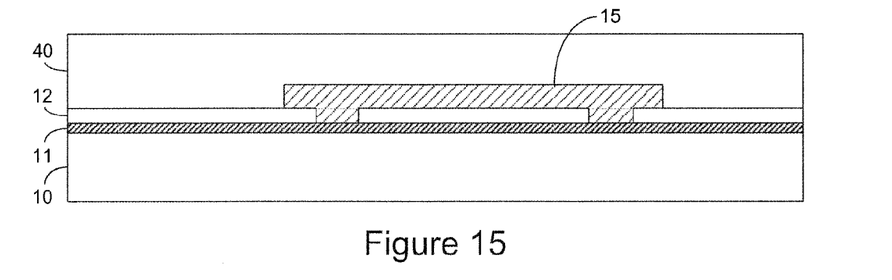
FIGS. 15-21 show the progression of fabricating a conformally encapsulated electrode array, in a fourth example embodiment of the method and apparatus of the present invention.
Figure 16:
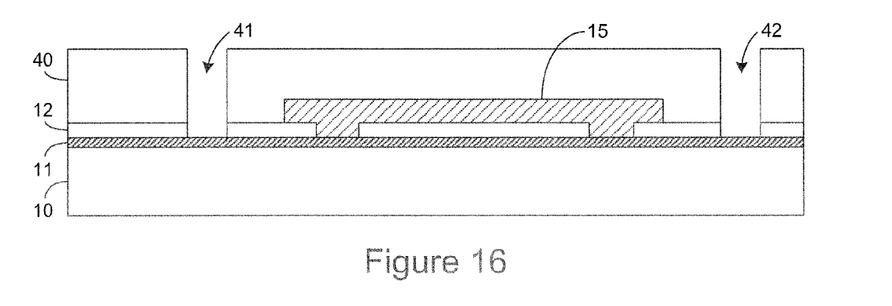

FIG. 15 shows a sacrificial material layer 40 formed over the patterned trace beam 15. The sacrificial material layer 40 may be the same or different material used for the sacrificial layer 12, which is selectively removable over the trace beam material. And FIG. 16 shows via openings 41 and 42 formed through the sacrificial material layer 40 and the sacrificial layer 12 down to the release layer 11, such as for example by an etching process.

Figure 17:
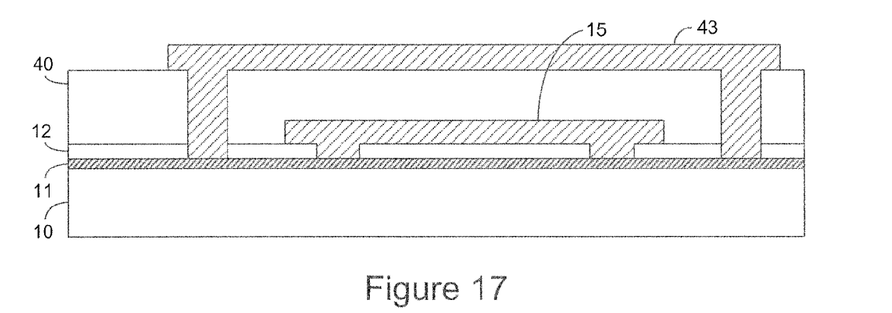

In FIG. 17, a second-tier trace beam 43 is formed (and patterned) on the sacrificial material layer 40, as well as in the via openings 41 and 42 to contact the release layer 11 therein. Furthermore, higher-tier sacrificial/scaffold layers and trace beams may be additionally provided as well. As can be seen in FIG. 17, the sacrificial material layer 40 (as well as the sacrificial layer 12) may be characterized as scaffolds which are temporarily provided on which to form and erect the suspended trace beam or beams as described herein, but which are subsequently removed when the support is no longer needed. While not shown in the drawings, it is also appreciated that additional vias may be formed between the suspension span portions of the tiered trace beams to form conductive interconnects between the trace beams.

Figure 18:
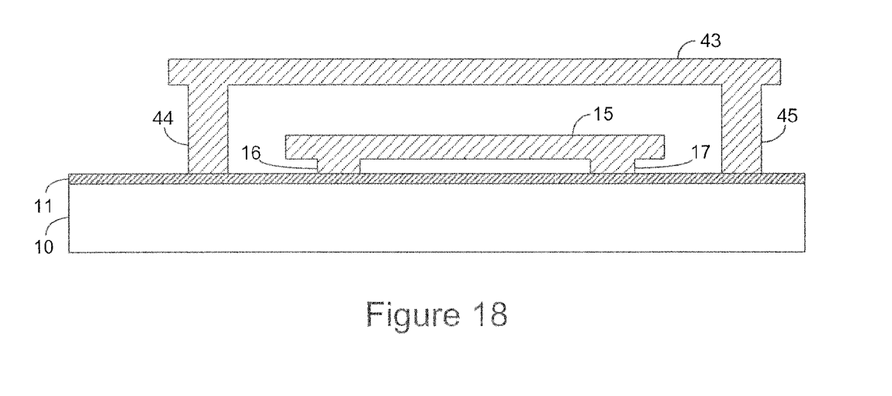

As shown in FIG. 18, the removal of the scaffolds leaves behind two independently suspended trace beams 43 and 15. Trace beam 43 has support legs 44 by which the trace beam is suspended over the substrate, and trace beam 15 has support legs 16 and 17 by which it is suspended over the substrate. It is appreciated, that though not shown, each of the trace beams may have been provided with single or double-sided trace backing for suspension support.

Figure 19:
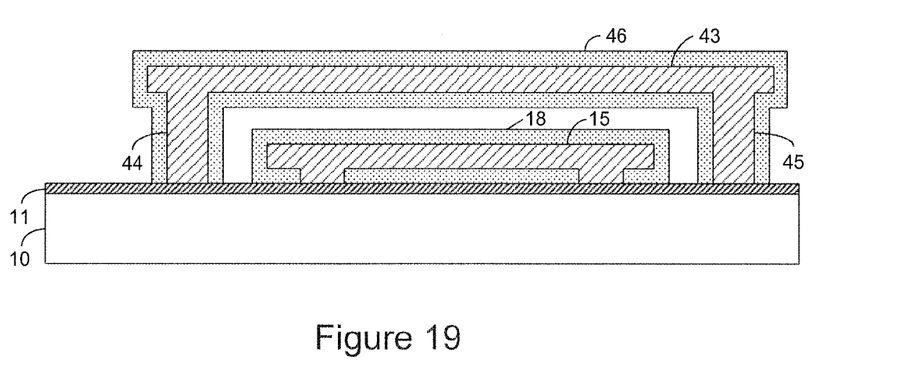

Next in FIG. 19, the independently suspended trace beams 43 and 15 are shown individually conformally encapsulated with an insulating material, indicated at 46 for beam 43, and indicated at 18 for beam 15. However, the insulating material 43 and 18 may be the same material deposited in a single vapor deposition step.

Figure 20:
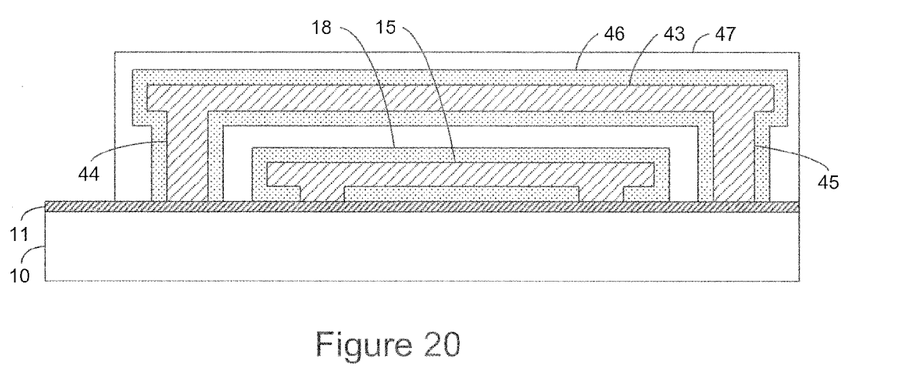
Figure 21:
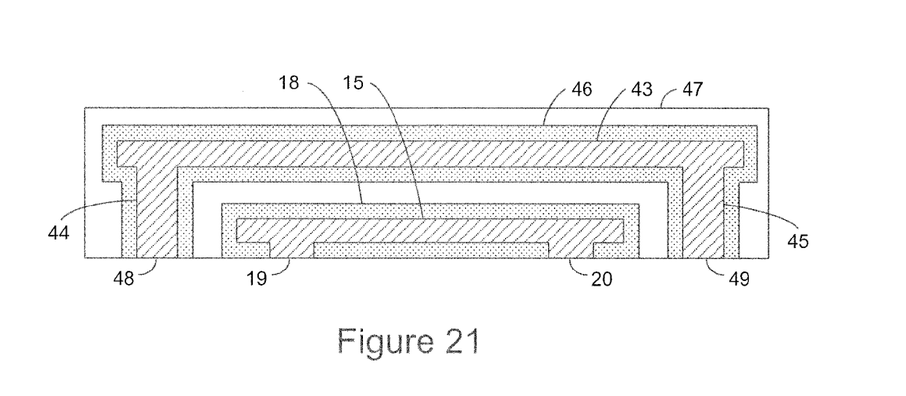

And FIG. 20 shows the setting of the two individually encapsulated trace beams together in a second insulating material 47, such as for example, silicone. The second insulating material 47 may be cast or otherwise shaped into a final shape/structure for an intended application, such as for example a probe structure for neural probe applications. The combined electrode array structure encapsulated in the insulating material 47, is then shown release from the substrate in FIG. 21, to expose conductive surfaces 48 and 49 of trace beam 43, and conductive surfaces 19 and 20 of trace beam 15.

FIGS. 22-27 show the progression of fabricating a conformally encapsulated electrode array, in a fifth example embodiment of the method and apparatus of the present invention. In particular, the progression of FIGS. 22-27 continues from the stage of fabrication shown in FIG. 11 and previously described, and show multiple traces which are stack-formed together with suspension support/backing layers therebetween, and suspended together as a multi-tier trace beam stack, and encapsulated as a multi-tier trace beam stack. As previously described the trace backing may be a thin layer of polymer deposited on a thin-film metal trace. And the polymer may be selected from various types of polymers.

Figure 22:
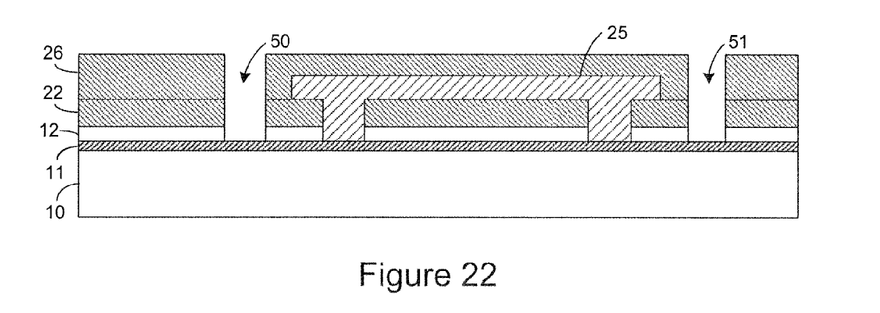
FIGS. 22-27 show the progression of fabricating a conformally encapsulated electrode array, in a fifth example embodiment of the method and apparatus of the present invention.

In particular, FIG. 22 shows two via openings 50 and 51 formed through the trace backing layers 26 and 22, and the sacrificial layer 12 down to the release layer 11, such as for example by an etching process. As previously described the sacrificial layer may be selected from various types of materials that may be selectively removed over the electrically conductive trace beam material 15.

Figure 23:
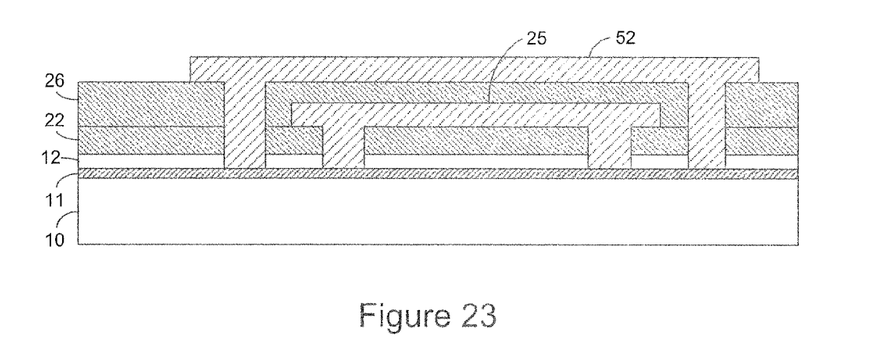
Figure 24:
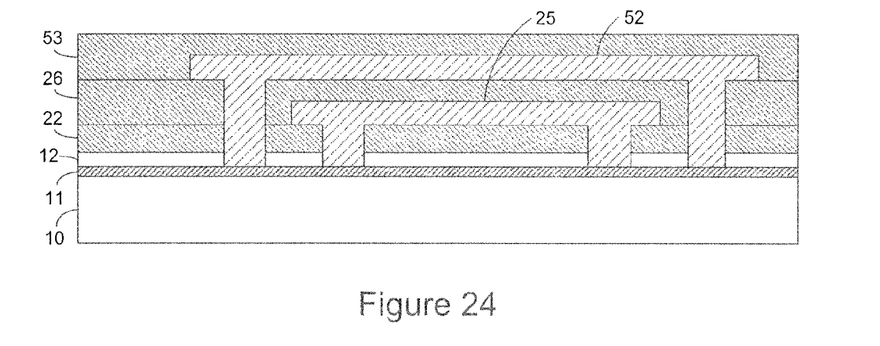

In FIG. 23, a second-tier trace beam 52 is formed (and patterned) on the trace backing layer 26, as well as in the via openings 50 and 51 to contact the release layer 11 therein. And FIG. 24 shows a third trace backing layer 53 formed on the second-tier trace beam 52, as well as partially on the second trace backing layer 26. In this manner, the trace beams are embedded within and reinforced by the trace backings. Furthermore, higher-tier trace backing layers and trace beams may be additionally provided as well to form a multi-tier trace beam stack structure that is reinforced with trace backing for suspension support.

Figure 25:
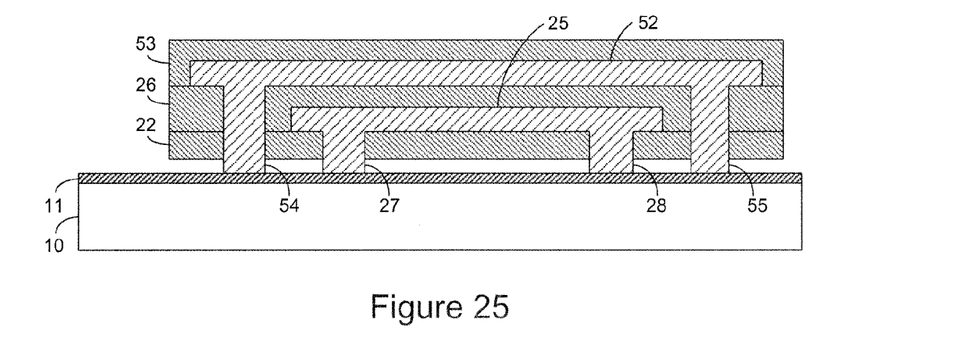
Figure 26:
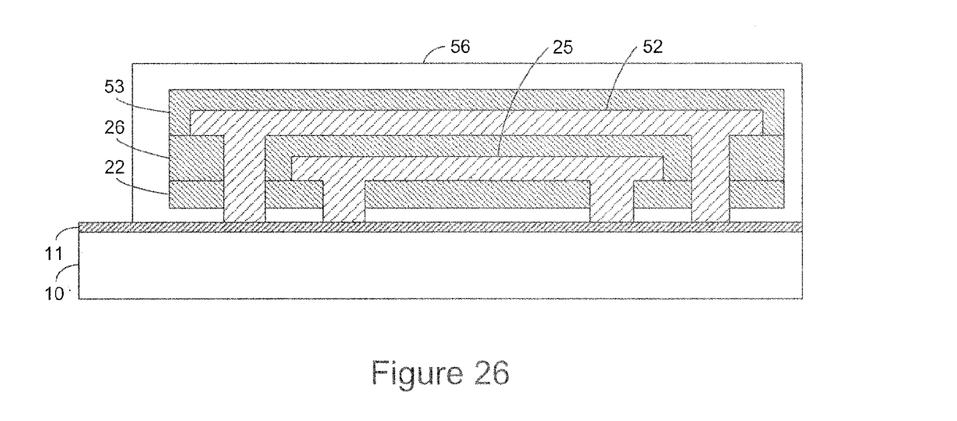
Figure 27:
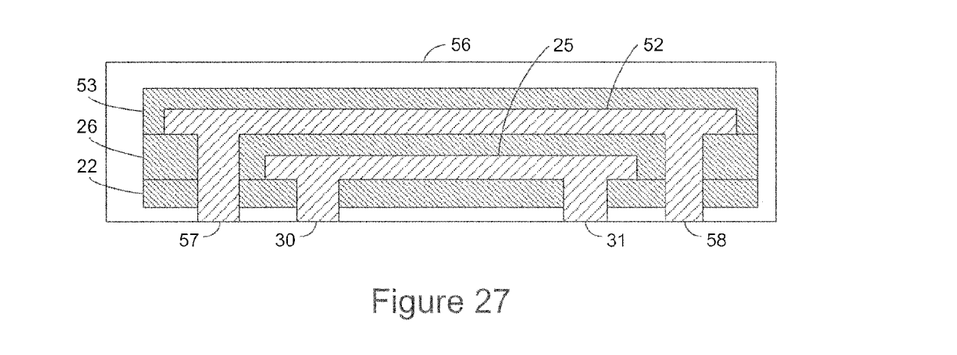

FIG. 25 shows removal of the sacrificial layer 12 (as previously described) to suspend the multi-tier trace beam stack over the substrate as a combined unit structure. In particular, the unit structure is suspension supported by support legs 54 and 55 of trace beam 52, and by support legs 27 and 28 of trace beam 25. While in the suspended state, the multi-tier trace beam stack (or simply the trace beam structure) is conformally encapsulated with a single layer of insulating material, as shown in FIG. 26. As shown in FIG. 26, the encapsulating coats all exposed surfaces of the trace beam structure, including between the trace backing 22 and the release layer 11. And FIG. 27 shows the trace beam structure released from the substrate, to expose conductive surfaces 57 and 58 of trace beam 52, and conductive surfaces 30 and 31 of trace beam 25.

Figure 28:
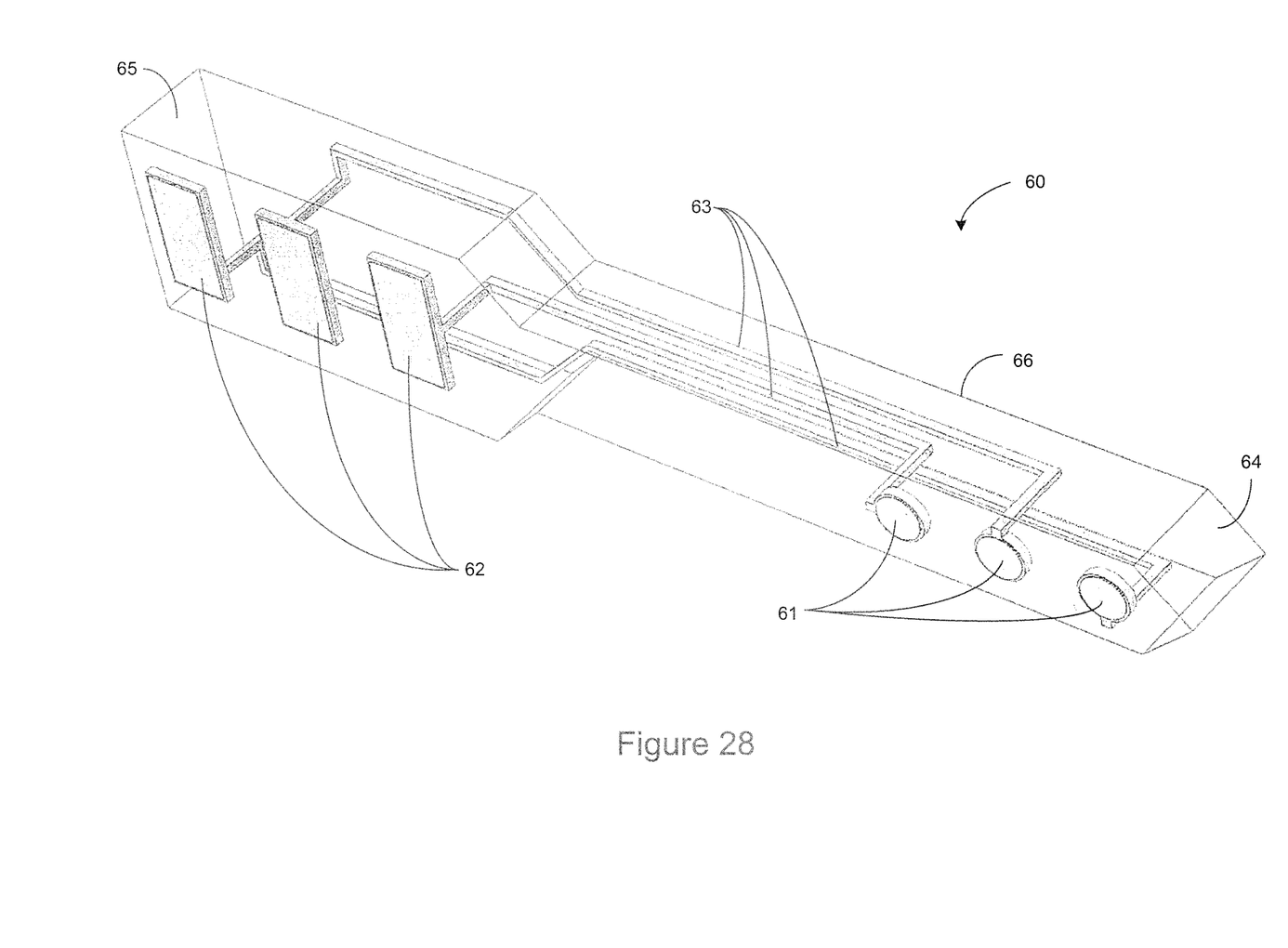
FIG. 28 shows an example neural probe fabricated according to the fabrication method of the present invention.

FIG. 28 shows an illustration of an example MEA construction fabricated according to the method of the present invention. In particular, a neural probe 60 is shown having an insertion end 64, and an opposite tail end 65. At the insertion end are shown three exposed electrodes 62 which are connected to three connector pads 62 at the tail end by respective traces 63. Each of the traces 63 are individually conformally encapsulate with an insulating material, and set together in a second insulating material 66, e.g. silicone, that is shaped into a probe structure.

Figure 29:
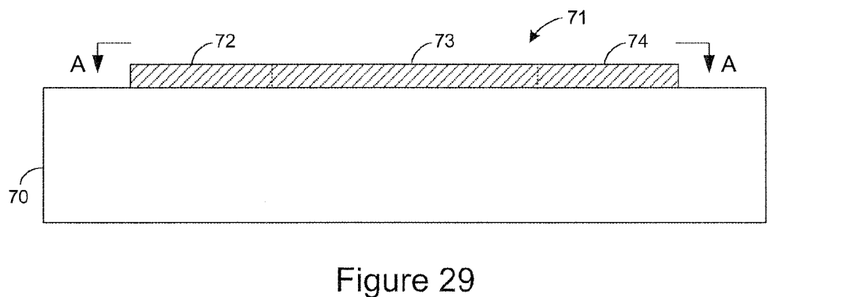
FIGS. 29-35 show the progression of fabricating a conformally encapsulated electrode array, in a sixth example embodiment of the method and apparatus of the present invention, with FIG. 30 viewed along line A-A of FIG. 29, and FIG. 32 viewed along line B-B of FIG. 31.
Figure 30:
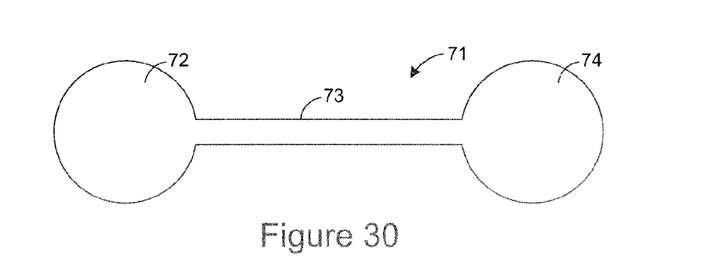
Figure 31:
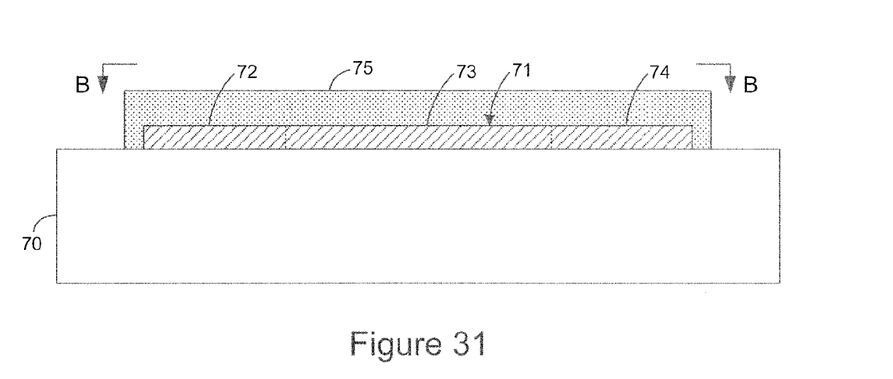
Figure 32:
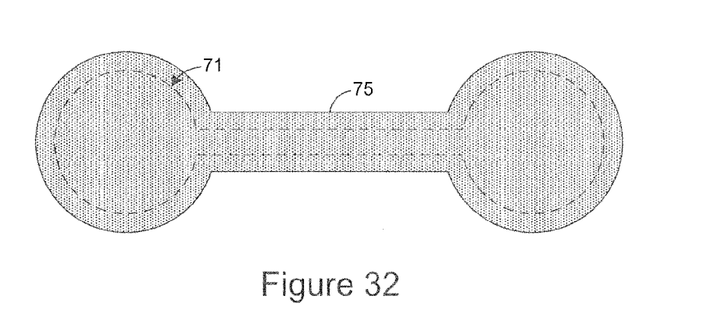

And FIGS. 29-35 show the progression of fabricating a conformally encapsulated electrode array, in a sixth example embodiment of the method and apparatus of the present invention. In particular, FIGS. 29 and 30 show a patterned conductive trace beam 71 formed on a substrate 70 and having opposing wide-area pad regions 72 and 74 which are connected by a narrow trace line 73 therebetween. And FIGS. 31 and 32 show a trace backing layer 75 that is deposited over the trace beam 71 to cover the trace beam and create an overhang extending beyond the outline of the trace beam. For example, the trace backing 75 may be parylene of about 1-5 µm thickness, and about 3-5 µm overhang.

Figure 33:
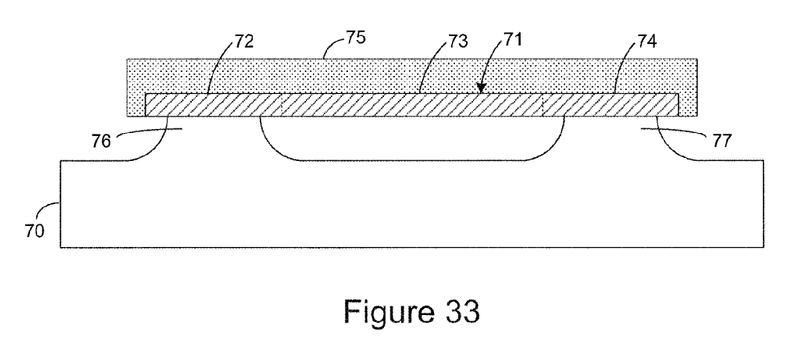

In FIG. 33 the substrate 70 is shown isotropically etched to completely undercut the trace beam 71 beneath the suspension span portion, i.e. the trace line 73, while portions of the substrate beneath the wide-are pad regions 72 and 74 remain unetched and in contact with the pad regions. In this regard, the substrate may be a silicon substrate and etched with an etchant selective to Si over metal. Furthermore, the trace backing 72 may serve as an etch mask. It is appreciated that the upright substrate formation beneath the pad regions may be characterized as substrate columns 76 and 77, and the pad regions 72 and 74 may be characterized as the support portions of the trace beam 71 by which the trace beam is suspended over the substrate.

Figure 34:
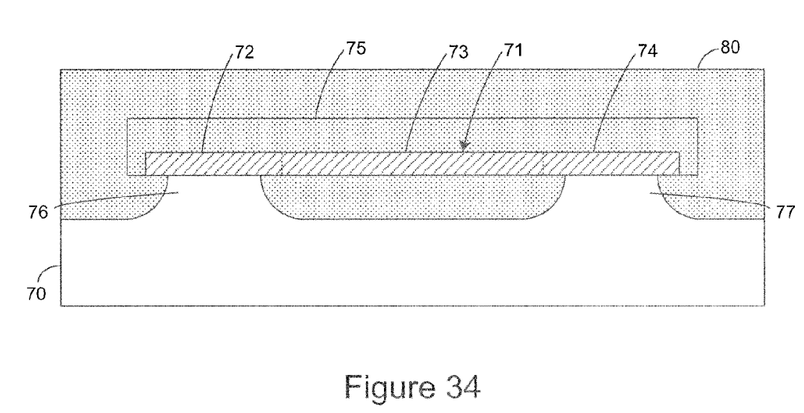
Figure 35:
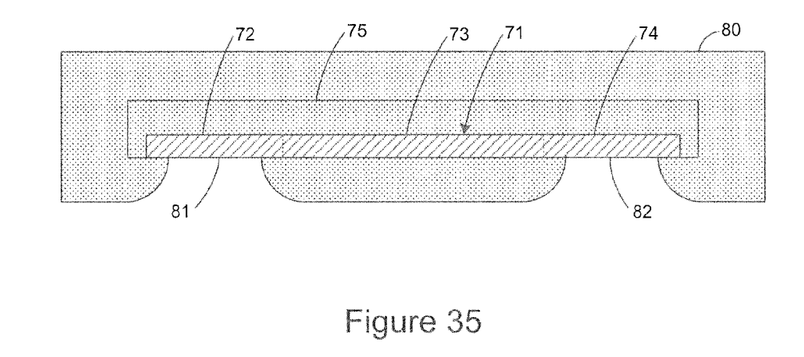

In FIG. 34, the reinforced and suspended trace beam 71 (and trace backing 75) are conformally encapsulated with an insulating material, such as for example parylene, as previously described, and may be subsequently patterned. As can be seen in FIG. 34 the conformal encapsulation coats all exposed surfaces of the suspended trace beam structure, including underneath the beam between the substrate. Next in FIG. 35, the conformally encapsulated trace beam (or beams, in an electrode array) is released from the substrate 70, so that conductive surfaces 81 and 82 of the wide-area pads 72 and 74 respectively of the trace beam are exposed. For an Si substrate, the releasing step may be performed, for example, by isotropic etch of the entire remaining wafer.

While particular operational sequences, materials, temperatures, parameters, and particular embodiments have been described and or illustrated, such are not intended to be limiting. Modifications and changes may become apparent to those skilled in the art, and it is intended that the invention be limited only by the scope of the appended claims.

We claim:

1. An electrode array comprising:
   at least one thin-film electrically conductive trace beam(s) suspension-encapsulated in a seamless single deposition-formed coating of electrically insulating material so that the coating continuously and conformably covers all surfaces of the trace beam(s) except an electrically conductive surface of at least one support portion(s) of the encapsulated trace beam(s) which is exposed through the coating.

2. The electrode array of claim 1,
   wherein the support portion(s) is a via-formed post(s) extending through the seamless coating.

3. The electrode array of claim 1,
   further comprising at least one trace backing(s) reinforcing the trace beam(s) to form at least one trace beam structure(s), and wherein the trace beam structure(s) is suspension-encapsulated in the seamless coating.

4. The electrode array of claim 3,
   wherein the trace backing(s) and multiple trace beams form a multi-tiered trace beam structure that is suspension-encapsulated in the seamless coating.

5. The electrode array of claim 3, further comprising at least one adhesion layer(s) between the trace beam structure(s) and the seamless coating.

6. The electrode array of claim 1, further comprising a second electrically insulating material connecting at least two independently suspension-encapsulated trace beams together.

7. The electrode array of claim 1, further comprising an adhesion promoting layer between the trace beam(s) and the seamless coating.

* * * * *